United States Patent [19]
Campbell et al.

[11] Patent Number: 5,958,430
[45] Date of Patent: Sep. 28, 1999

[54] THIN FILM COMPOSITION WITH BIOLOGICAL SUBSTANCE AND METHOD OF MAKING

[75] Inventors: Allison A. Campbell, Kennewick; Lin Song, Richland, both of Wash.

[73] Assignee: Battelle Memorial Institute, Richland, Wash.

[21] Appl. No.: 09/026,748

[22] Filed: Feb. 20, 1998

[51] Int. Cl.$^6$ .............. A61K 9/00; A61F 13/00; A61F 2/00
[52] U.S. Cl. .......... 424/400; 424/422; 424/423; 424/426
[58] Field of Search ................ 424/400, 422, 424/423, 426; 623/16; 523/113, 114, 115; 428/426, 457

[56] References Cited

U.S. PATENT DOCUMENTS 5,591,453  1/1997  Ducheyne et al. ............ 424/484

OTHER PUBLICATIONS

Bunker et al, Ceramic thin–film formation on funtionalized interfaces through biomimetic processing, Science, vol;264, Apr. 1, 1994.

Rieke, P., et al, Biomimetic Thin–Film Synthesis, American Chemical Society Symposium, 1992, Series No. 499, Chapter 6, 61–75.

Campbell, A., et al, Bioactive Void Metal Composites for Orthopedic Implant Devices, Materials Research Society Symposium, 1996, vol. 414, 177–182.

Smith, P., Measurement of Protein Using Bicinchoninic Acid, *Analytical Biochemistry,* 1985, 150, 76–85.

*Primary Examiner*—Thurman K. Page
*Assistant Examiner*—Lakshmi Channavajjala
*Attorney, Agent, or Firm*—Paul W. Zimmerman

[57] ABSTRACT

The invention provides a thin-film composition comprising an underlying substrate of a first material including a plurality of attachment sites; a plurality of functional groups chemically attached to the attachment sites of the underlying substrate; and a thin film of a second material deposited onto the attachment sites of the underlying substrate, and a biologically active substance deposited with the thin-film. Preferably the functional groups are attached to a self assembling monolayer attached to the underlying substrate. Preferred functional groups attached to the underlying substrate are chosen from the group consisting of carboxylates, sulfonates, phosphates, optionally substituted, linear or cyclo, alkyl, alkene, alkyne, aryl, alkylaryl, amine, hydroxyl, thiol, silyl, phosphoryl, cyano, metallocenyl, carbonyl, and polyphosphate. Preferred materials for the underlying substrate are selected from the group consisting of a metal, a metal alloy, a plastic, a polymer, a proteic film, a membrane, a glass or a ceramic. The second material is selected from the group consisting of inorganic crystalline structures, inorganic amorphus structures, organic crystalline structures, and organic amorphus structures. Preferred second materials are phosphates, especially calcium phosphates and most particularly calcium apatite. The biologically active molecule is a protein, peptide, DNA segment, RNA segment, nucleotide, polynucleotide, nucleoside, antibiotic, antimicrobal, radioisotope, chelated radioisotope, chelated metal, metal salt, anti-inflamatory, steriod, nonsteriod anti-inflammatory, analgesic, antihistamine, receptor binding agent, or chemotherapeutic agent, or other biologically active material. Preferably the biologically active molecule is an osteogenic factor the compositions listed above.

25 Claims, No Drawings

THIN FILM COMPOSITION WITH BIOLOGICAL SUBSTANCE AND METHOD OF MAKING

This invention was made with Government support under Contract DE-AC06 76RLO 1830 awarded by the U.S. Department of Energy. The Government has certain rights in the invention.

FIELD OF THE INVENTION

This invention provides a thin-film coating incorporating biologically active materials.

BACKGROUND OF THE INVENTION

A method for depositing thin film layers on to surfaces modified with organic functional groups and products formed thereby is disclosed in published PCT application WO 91/17286. Refinements of the method are disclosed in Bunker, et als. *Ceramic Thin Film Formation on Functionalized Interfaces Through Biomemetic Processing*, Science, 264, 48–55 (1994) and Rieke, et als, *"Biomemetic Thin-Film Synthesis"*, in *Supramolecular Architecture: Synthetic Control in Thin-Films and Solids*, T Bein ed., American Chemical Society, Washington D.C., 61–75, (1992), and in "Bioactive Void Metal Compositites For Orthopedic Implant Devices," Campbell, et als., National Research Society Proceedings, 414, 177, (1996).

In the process for providing a film product, an underlying substrate of a first material is chemically modified on at least one surface by attaching functional groups which provide nucleation sites for inducing crystallite growth of an inorganic second material on the underlying substrate, and contacting at least one chemically modified surface with a liquid solution of precursors of the inorganic second material for a sufficient period of time for the crystallite growth of a second material formed from the precursors of the inorganic second material in the liquid solution onto the modified underlying substrate by nucleation of the second material on the nucleation sites thereby forming inorganic crystallite second material growth onto the nucleation sites, the nucleation sites being chemically attached to the underlying substrate. Materials that mimic biological materials such as porous metal composites coated with hydroxyapatite have been produced by this process.

Processes for delivery of biologically active molecules such as bone morphogenic proteins have also been previously disclosed. See for example U.S. Pat. No. 5,385,887 and references cited therein. However the incorporation of biologically active materials, such as proteins into thin-film coatings has not previously been demonstrated. Release of such incorporated materials has not previously been suggested.

SUMMARY OF THE INVENTION

The invention provides thin-film composition comprising an underlying substrate of a first material including a plurality of attachment sites; a plurality of functional groups chemically attached to the attachment sites of the underlying substrate; and a thin film of a second material deposited onto the attachment sites of the functional groups, and a biologically active substance deposited with the thin-film. Preferably a self assembling monolayer containing functional groups is attached to the underlying substrate. Preferred functional groups attached to the underlying substrate are chosen from the group consisting of carboxylates, sulfonates, optionally substituted, linear or cyclo, alkyl, alkene, alkyne, aryl, alkylaryl, amine, hydroxyl, thiol, silyl, phosphoryl, cyano, metallocenyl, carbonyl, phosphates and polyphosphates. Preferred materials for the underlying substrate are selected from the group consisting of a metal, a metal alloy, a plastic, a polymer, a protein film, a membrane, a glass or a ceramic. The second material is selected from the group consisting of inorganic crystalline structures, inorganic amorphus structures, organic crystalline structures, and organic amorphus structures. Preferred second materials are phosphates, especially calcium phosphates and most particularly octacalcium phosphates ("OCP"). Especially preferred are componds selected from the group consisting of octacalcium phosphate, hydroxyapatite and carbonate apatite.

The biologically active molecule is a protein, peptide, DNA segment, RNA segment, nucleotide, polynucleotide, nucleoside, antibiotic, antimicrobal, radioisotope, chelated radioisotope, chelated metal, metal salt, anti-inflammatory, steroid, nonsteroid anti-inflammatory, analgesic, antihistamine, receptor binding agent, or chemotherapeutic agent, or other biologically active material. Preferably the biologically active molecule is an osteogenic factor. In an alternative embodiment the invention may be described as a method for preparing a multi component coating which comprises treating a first material to produce a plurality of attachment sites on its surface, attaching a plurality of functional groups to the attachment sites, incorporating the functional groups into a thin-film of a second material deposited onto the material and providing a biologically active material which is incorporated into the thin film deposited onto the material. The method is suitable for providing all the compositions listed above.

In alternative embodiments the invention provides a bone fixation device and a method for delivery of drugs or therapeutic agents.

DETAILED DESCRIPTION OF THE INVENTION

While the prior art has provided thin-film deposition methods, and compositions for drug delivery or sustained release, the art has not provided a method for depositing thin-films incorporating biologically active substances. The present work demonstrates that useful thin-films incorporating biologically active substances can be deposited by a variation of the method disclosed in published PCT application WO 91/17286. Small molecules, such as antibiotic and anti-cancer drugs, and proteins such as bovine serum albumin and transforming growth factor β1 have been successfully incorporated into calcium phosphate coatings on titanium and titanium alloy surfaces modified using self assembling monolayers. The preparation of these examples is set out in detail below.

EXAMPLE 1

Surface Functionalization Using Self Assembling Monolayers (SAM)

Prior to SAM formation, titanium or titanium alloy wafers were cut and polished on one side. The wafers were placed on racks and washed with acetone and ethanol. After being sonicated in chloroform for 2–3 minutes, the wafers were exposed to an air plasma for 20 minutes to remove organic residues. The wafers were treated with 0.1M KOH for 2 minutes. The wafers were then immersed in 0.1M $HNO_3$ for 10 minutes. The wafers were blown dry after a thorough washing with deionized water. The wafers were further dried in a nitrogen stream for 2 hours. The self assembling monolayers were formed by treating the wafers in a 0.5 wt % terminal alkenyl-silane such as 1-(trichlorosilyl)-undec-10-ene in cyclohexane solution for 30 minutes. The wafers were rinsed in 2-propanol, sonicated in chloroform for 5 minutes and blown dry with nitrogen. The terminal vinyl group of the alkenyl silane was converted to a sulfonic acid by exposure to $SO_3$ gas for 1 minute. Following sulfonation the wafers were sonicated in deionized water for 10 minutes and blown dry with nitrogen.

EXAMPLE 2

Calcium Phosphate Film Deposition

A supersaturated calcium phosphate solution containing 5 mM $CaCl_2$, 1.5 mM $KH_2PO_4$ and 1.5 mM $Na_2HPO_4$ was prepared by mixing 1.5 ml of 0.1M $KH_2PO_4$ and 1.5 ml of 0.1M $Na_2HPO_4$ stock solutions into 92 ml of deionized water, followed by the slow addition of 5.0 ml 0.1M $CaCl_2$ solution. The combined solution was stirred for 3 minutes and derivatized wafers prepared as in Example 1 above, were immersed in the solution and taken out just before the solution precipitated (about one hour). The wafers were then rinsed with deionized water and blown dry with nitrogen. The process may be repeated several times to achieve a desired thickness. Films up to 20 microns were obtained in this way. The resulting calcium phosphate films were characterized by X-ray diffraction and scanning electron microscopy. The thin film prepared as described showed a single phase of octacalcium phosphate.

EXAMPLE 3

Incorporation and Release of Protein and Drug Molecules by Calcium Phosphate Films Stock solutions of 5.6 mg/ml of 5 fluro-uracil (5-FU), 1 mg/ml tetracycline, 0.65 mg/ml bovine serum albumin (BSA) and 0.33 μg/ml transforming growth factor -β1 (TGF-β1) were prepared and adjusted to pH 6.5 before use. After a calcium phosphate deposition cycle as described in Example 2, wafers were immersed in the desired stock solution for 1 hour, rinsed and blown dry (one adsorption cycle). If desired additional calcium phosphate deposition as described in Example 2 may be carried out followed by additional adsorption from stock solution. Stock solution concentrations were determined before and after each adsorption cycle and the amount adsorbed was determined by the deference. Concentrations of incorporated sample and released materials are tabulated below. Concentrations of 5-FU were determined by direct measurement of the adsorption at 266 nm. BSA was determined by the bicinchonic acid method, P. K. Smith, et al., "Measurement of Protein using Bicinchonic Acid," Analytical Biochemistry, 150, 76–85 (1985), and by adsorption at 562 nm. Concentration of TGF-β1 was determined by the Quantikine immunoassay, (R&D Systems). Tetracycline concentrations were determined by adsorption at 275 nm.

TABLE 1

TGF-β1 absorbed into calcium phosphate film as a function of absorption cycles

| Adsorption Cycles | TGF-β1 Absorpbed ($\mu/cm^2$) |
| --- | --- |
| 0 | 0 |
| 1 | 0.00686 |
| 2 | 0.260 |
| 3 | 0.374 |
| 4 | 0.400 |
| 5 | 0.404 |
| 6 | 0.407 |

Release of Incorporated Proteins and Drugs

Wafer samples processed several times as described above were placed in 0.1M NaCl (saline) solution at 25° C. Wafers were periodically transferred to fresh saline and the concentration in the old saline was measured directly as in Example 3 by evaporating to dryness then analyzing. Table 2 shows release of 5-FU and Table 3 shows release of BSA.

TABLE 2

5-FU release in 0.15M NaCl at 25° C. from a 5 Micron Thick OCP Film

| Time (hours) | 5-FU Released ($\mu/cm^2$) |
| --- | --- |
| 0 | 0 |
| 0.133 | 0.004 |
| 0.250 | 0.008 |
| 0.367 | 0.012 |
| 6.00 | 0.193 |
| 22.00 | 0.707 |
| 27.50 | 0.884 |
| 46.50 | 1.495 |
| 73.00 | 2.347 |
| 77.00 | 2.476 |
| 143.00 | 4.598 |
| 167.00 | 5.370 |

EXAMPLE 4

Direct Incorporation

The procedure of Example 2 is repeated and a selected drug such as tetracycline or 5 fluorouracil, a DNA segment, or a protein such as TGF-β1 is slowly added with the $CaCl_2$ by titration. In this manner the adsorption and deposition occur at the same time. This procedure can be used with any biologically active molecule that can be dissolved or suspended in the $CaCl_2$ solution. Insoluble or unstable molecules may be adsorbed as in Example 3.

TABLE 3

BSA Release from OCP films in 0.15M NaCl at 25° C.

| Time (hour) | BSA Released ($mg/m^2$) |
| --- | --- |
| 0 | 0 |
| 0.25 | 0.0014 |
| 0.67 | 0.0011 |
| 1.67 | 0.0015 |
| 2.67 | 0.0019 |
| 4.67 | 0.0024 |
| 20.00 | 0.0042 |
| 28.00 | 0.0042 |
| 44.00 | 0.0065 |
| 167.00 | 0.0062 |

Any biologically active molecule may be deposited into the film using the technique of either example 3 or example 4. The method can be used for example to incorporate molecules of any of the following examples onto or into the film layer: a protein, peptide, DNA segment, RNA segment, nucleotide, polynucleotide, nucleoside, antibiotic, antimicrobial, radioisotope, chelated radioisotope, chelated metal, metal salt, anti-inflamatory, steriod, nonsteriod anti-inflammatory, analgesic, antihistamine, receptor binding agent, or chemotherapeutic agent. The film may be any organic or inorganic film that can be deposited on a functionalized surface. The surface may be any material having attachment sites for organic functional groups. The attachment sites may be generated or may be natural to the material. Any functional group that will support deposition of a second material may be used. The preferred materials are biologically compatible alloys suitable for implantation into humans, particularly porous metal implants of titanium or titanium alloys.

DEFINITIONS

"Biologically active substance means a substance that produces a detectable result other than a foreign body response when placed in contact with a living organism.

We claim:

1. In a thin-film composition comprising an underlying substrate of a first material including a plurality of attachment sites; a plurality of functional groups chemically attached to the attachment sites of the underlying substrate; and a thin film of a second material deposited onto the attachment sites of the underlying substrate, the improvement comprising a biologically active substance incorporated with the thin film of the second material.

2. A composition according to claim 1 wherein a self assembling monolayer containing functional groups are attached to the underlying substrate.

3. A composition according to claim 1 wherein the functional group attached to the underlying substrate is chosen from the group consisting of carboxylates, sulfonates, phosphates, optionally substituted, linear or cyclo, alkyl, alkene, alkyne, aryl, alkylaryl, amine, hydroxyl, thiol, silyl, phosphoryl, cyano, metallocenyl, carbonyl, and polyphosphate.

4. A composition according to claim 1 wherein the underlying substrate is selected from the group consisting of a metal, a metal alloy, a polymer, a protein film, a glass or a ceramic.

5. A composition according to claim 1 wherein the second material is selected from the group consisting of inorganic crystalline structures, inorganic amorphous structures, organic crystalline structures, and organic amorphous structures.

6. A composition according to claim 5 wherein the second material is a phosphate.

7. A composition according to claim 5 wherein the second material is a calcium phosphate.

8. A composition according to claim 5 wherein the second material is selected from the group consisting of octacalcium phosphate, hydroxyapatite and carbonate apatite.

9. A composition according to claim 1 wherein the biologically active molecule is a protein, peptide, DNA segment, RNA segment, nucleotide, polynucleotide, nucleoside, antibiotic, antimicrobial, radioisotope, chelated radioisotope, chelated metal, metal salt, anti-inflammatory, steroid, nonsteroid anti-inflammatory, analgesic, antihistamine, receptor binding agent, or chemotherapeutic agent.

10. A composition according to claim 1 wherein the biologically active molecule is an osteogenic factor.

11. A composition of matter comprising a first porous metal material having a surface and attachment sites located on the surface and a self assembling mono layer containing functional groups provided at attachment sites, and a second crystallite calcium phosphate material nucleated by a functional group at an attachment site and grown as a dense film on the surface of the first material the calcium phosphate having an osteogenic factor incorporated therein.

12. A method for preparing a multi component coating which comprises treating a first material to produce a plurality of attachment sites on its surface, attaching a plurality of functional groups to the attachment sites, incorporating the functional groups into a thin-film of a second material deposited onto the material and providing a biologically active material which is incorporated onto or into the thin film deposited on the first material.

13. A method according to claim 12 wherein the treating step provides attachment sites to which a self assembling mono-layer can be attached.

14. A method according to claim 12 wherein the functional group attached to the attachment sites is chosen from the group consisting of carboxylates, sulfonates, phosphates, optionally substituted, linear or cyclo, alkyl, alkene, alkyne, aryl, alkylaryl, amine, hydroxyl, thiol, silyl, phosphoryl, cyano, metallocenyl, carbonyl, and polyphosphate.

15. A method according to claim 12 wherein the first material is selected from the group consisting of a metal, a metal alloy, a polymer, a protein film, a glass or a ceramic.

16. A method according to claim 12 wherein the second material is selected from the group consisting of inorganic crystalline structures, inorganic amorphous structures, organic crystalline structures, and organic amorphous structures.

17. A method according to claim 16 wherein the second material is a phosphate.

18. A method according to claim 16 wherein the second material is a calcium phosphate.

19. A method according to claim 16 wherein the biologically active molecule is a protein, peptide, DNA segment, RNA segment, nucleotide, polynucleotide, nucleoside, antibiotic, radioisotope, chelated radioisotope, chelated metal, metal salt, anti-inflamatory, steriod, nonsteriod anti-inflammatory, analgesic, antihistamine, receptor binding agent, or chemotherapeutic agent.

20. A method according to claim 16 wherein the biologically active molecule is an osteogenic factor.

21. An implant for use in a mammalian body comprising a composition according to claim 1.

22. A method for delivery of a biologically active substance which comprises treating an implant according to claim 12 and implanting the implant at a site to which the biologically active substance is to be delivered.

23. A bone fixation device comprising a composition according to claim 1.

24. A bone fixation device according to claim 23 wherein the biologically active molecule is an osteogenic factor.

25. A bone fixation device according to claim 23 wherein the first material is porous.

* * * * *

UNITED STATES PATENT AND TRADEMARK OFFICE
CERTIFICATE OF CORRECTION

PATENT NO. : 5,958,430
DATED : September 28, 1999
INVENTOR(S) : Campbell et al.

It is certified that error appears in the above-identified patent and that said Letters Patent is hereby corrected as shown below:

<u>Column 3,</u>
Line 67, please replace "0.1M" with -- 0.15M --.

Signed and Sealed this

Twenty-fifth Day of February, 2003

JAMES E. ROGAN
*Director of the United States Patent and Trademark Office*